United States Patent [19]

Lynn

[11] 4,072,566
[45] Feb. 7, 1978

[54] IMMOBILIZED BIOLOGICALLY ACTIVE PROTEINS

[75] Inventor: Merrill Lynn, Big Flats, N.Y.
[73] Assignee: Corning Glass Works, Corning, N.Y.
[21] Appl. No.: 726,592
[22] Filed: Sept. 27, 1976
[51] Int. Cl.$^2$ .............................................. C07G 7/02
[52] U.S. Cl. ...................................... 195/63; 195/68; 195/DIG. 11; 260/112 R
[58] Field of Search .................. 195/63, 68, DIG. 11; 260/112 R

[56] References Cited

U.S. PATENT DOCUMENTS

| 3,669,841 | 6/1972 | Miller ................................. | 195/63 |
| 3,873,426 | 3/1975 | Katchalski et al. ................. | 195/63 |
| 3,930,951 | 1/1976 | Messing ............................. | 195/63 |
| 3,983,000 | 9/1976 | Messing et al. .................... | 195/63 |

OTHER PUBLICATIONS

Gray et al., A New and Convenient Method for Enzyme Insolubilisation Using Diazotized M-Diaminobenzene, Biochimicz et Biophysica Acta, vol. 341, 1974, (pp. 457–464).

Primary Examiner—David M. Naff
Attorney, Agent, or Firm—James A. Giblin; Clinton S. Janes, Jr.; Clarence R. Patty, Jr.

[57] ABSTRACT

Arylamine surface derivatives useful for the immobilization of biologically active proteins such as enzymes can be prepared by adsorbing p-phenylenediamine onto the surfaces of water-insoluble inorganic carriers having a relatively low surface isoelectric point.

6 Claims, No Drawings

IMMOBILIZED BIOLOGICALLY ACTIVE PROTEINS

BACKGROUND OF THE INVENTION

This disclosure relates generally to the field of immobilized proteins and is specifically concerned with a novel method of attaching usefully active proteins such as enzymes to the surfaces of a variety of inorganic support materials.

The desirability of attaching useful proteins such as enzymes, antibodies, and the like onto insoluble support materials is well known. In general the immobilization of such biologically active materials results in insoluble composite materials which can be reused and/or easily separated from a reaction medium.

A wide variety of materials has been used successfully as support or carrier materials for proteins. The carriers may be organic (e.g. U.S. Pat. No. 3,645,852), inorganic (e.g. U.S. Pat. No. 3,556,945), or a combination of the two (e.g. 3,705,084). Various modes of attachment include simple adsorption, entrapment, and chemical coupling of the proteins to the carrier surfaces.

Recent studies have shown that for many applications, inorganic carriers are preferable to organic materials and the various advantages are described and/or demonstrated in several relatively recent patents (e.g. U.S. Pat. No. 3,556,945; describing the adsorption of enzymes to porous glass; U.S. Pat. No. 3,519,538, describing the covalent bonding of enzymes to silanized inorganics; U.S. Pat. No. 3,562,761, describing the covalent bonding of antibodies to silanized inorganics; and U.S. Pat. No. 3,850,751, describing the adsorption of enzymes to a variety of non-siliceous inorganics such as alumina, titania, and the like).

Much of the early work with inorganic carriers involved using those materials to simply adsorb proteins from a solution. Although that technique of bonding has many obvious advantages, it was apparent that the actual bonding forces were relatively weak and pH dependent, thus limiting the use of adsorbed protein systems. It should be noted, however, that some adsorbed enzyme systems have been shown to be highly useful. See, for example, U.S. Pat. No. 3,868,304, disclosing the use of glucose isomerase adsorbed to highly porous alumina particles to isomerize glucose to fructose.

In an effort to remedy some of the disadvantages of adsorbed enzymes, attempts were made to covalently bond non-essential portions of protein molecules to various carriers. In the case of inorganic supports, it was found that silane coupling agents could be used as an intermediate link between the inorganic surface and the protein (see U.S. Pat. No. 3,519,538, enzymes, and U.S. Pat. No. 3,652,761, antibodies). The resulting composites possessed the known advantages of inorganic carriers and demonstrated a relatively stronger bonding of the proteins. Although silane coupling agents can be used to bond a wide variety of materials to inorganics, they are relatively few in number and, in some cases, relatively expensive. Also, their use requires several processing steps. For example, after attachment to an inorganic surface (e.g., glass) it is often necessary, depending on the silane used, to further functionalize the silane to render it suitable for covalent bonding.

Surprisingly, I have found that proteins can be attached to inorganic carriers by means of an adsorbed surface derivative. To the adsorbed surface derivative, a variety of proteins can be covalently bonded without loss of biological activity. Thus, the relative ease of adsorbing the coupling agent to an inorganic to produce a relatively strongly bonded surface derivative is combined with being able to subsequently bond a protein via covalent bonds to the derivatized surface. Details of the method are described herein.

SUMMARY OF THE INVENTION

The method of bonding biologically active proteins to the surfaces of inorganic support materials comprises the steps of:

a. reacting a high surface area, insoluble, inorganic support material having a relatively low surface isoelectric point with a solution of p-phenylenediamine, (1,4-diaminobenzene) under conditions sufficient to adsorb at least a portion of the p-phenylenediamine onto the surfaces of the support material;

b. separating the supporting material from the solution of the p-phenylenediamine and c. reacting the separated support material with a solution of proteins under conditions sufficient to assure the covalent bonding of at least a portion of the proteins to the support material without significant loss of biological activity. In various preferred embodiments, the surface derivatized support of step (a), after removal from the p-phenylenediamine solution, is further functionalized prior to reaction with the proteins. For example, the free amino groups of the derivatized surface can be readily modified via a diazotization step or Schiff base reaction (reaction with an aldehyde).

SPECIFIC EMBODIMENTS

The main requirements for the inorganic carriers are that they have a relatively high surface area ($> 10$ $m^2/g$) to assure relatively high loading of proteins; be relatively water insoluble; and, very importantly, have a relatively low surface isoelectric point. The isoelectric point of the surface is the pH at which the electrostatic surface potential (zeta potential) is zero. Isoelectric points of surfaces are described by G. A. Parks, Advances In Chemistry Series 67, 121-160 (1967), and G. A. Parks, Chemical Reviews 65, 177-198 (1964). The purpose of having a relatively low surface isoelectric point (less than pH 7.0) is to enhance the formation of strong electrostatic bonds between the acidic inorganic surface and the basic organic amine. Typical examples of inorganic carriers having low isoelectric points are siliceous materials such as glass and silica particles. Other suitable inorganics are stannic oxide, titania, manganese dioxide and zirconia (See G. A. Parks, Chemical Reviews 65, 177-198 (1964).

The p-phenylenediamine is commercially available and relatively inexpensive. The amine group at one end of the molecule adsorbs very strongly onto the surfaces of the carrier having a low isoelectric point and, once so adsorbed, the molecules are difficult to remove. The procedure differs from that used to attach silane coupling agents in that an amino group of the diamine is strongly adsorbed or electrostatically bonded to the surface rather than covalently reacted via available hydroxyl groups. (See E. P. Plueddemann and G. L. Stark, Proc. SPI 28th Am. Tech. Conf., Sec. 21-E (1973).) The second amine is available for subsequent coupling of the proteins.

The arylamine group is desirable for chemical coupling since it can be used for diazotization or, as described below, it can be readily modified to produce other reactive groups. As demonstrated in the examples below, a variety of enzymes were bonded via different reactive groups to the inorganic carriers.

PREPARATION OF ARYL AMINE GLASS DERIVATIVES

A series of arylamine glass derivatives was prepared in the following manner. Solutions of the diamine were prepared by dissolving one gram, five grams and ten grams of p-phenylenediamine in 100 ml of ethanol. To each of the diamine solutions was added ten grams of porous glass particles (40 to 80 mesh) having an average pore diameter of 550A. The reaction mixtures were shaken for 30 minutes at 60° C. The reaction solutions were decanted and the products were washed with ethanol until no more diamine could be removed (as indicated by color in the washes). The products were then washed with 0.5 M NaCl solution until the washings were colorless, followed by additional washing with water.

All three products gave positive tests for arylamine with the $\beta$-naphthol test. The products were analyzed for reactive amine loading by titration with perchloric acid.

TABLE I

| | Reactive Amine Loadings | |
|---|---|---|
| Sample Reaction Solution | % N | MEQ Amine/g |
| A. 1% (g/100 ml) | 0.29 | 0.21 |
| B. 5% (g/100 ml) | 0.33 | 0.23 |
| C. 10% (g/100 ml) | 0.46 | 0.33 |

EXAMPLE I IMMOBILIZATION OF PAPAIN BY AZO COUPLING

Papain was immobilized on the arylamine supports in the following manner. To one gram samples of the arylamine supports described above was added 10 ml of 2 N HCl and the reaction mixture was cooled in an ice bath. To the mixtures was added 2.5 ml of 4 M sodium nitrite solution, then the reaction mixtures were evacuated for 30 minutes to remove gas bubbles from the pores. The reaction solutions were decanted, and the products were washed several times with water.

Papain was coupled to the supports by adding one ml of a solution containing 100 mg of papain in pH 8.5 phosphate buffer to one gram of diazotized support. The reactions were allowed to continue for two hours in an ice bath, then the reaction solutions were decanted. The immobilized enzymes were washed for 15 minutes with 6 M urea solution, then with water, then for 30 minutes with 0.5 M sodium chloride solution, then several more times with water. The immobilized enzymes were stored under water in a refrigerator.

The immobilized enzymes were assayed with 1% casein solution in phosphate buffer at pH 7 containing cysteine and EDTA at 37° C. The enzyme loadings, reported as mg of active papain per gram of support are listed below. The immobilized enzymes were assayed again after storage for 83 days, and these results are also listed below.

TABLE II

| Carrier Sample | Immobilized Papain Activities | |
|---|---|---|
| | Enzyme Loading, mg Papain/g Support | |
| | Initial | 83 Days Storage |
| A | 31.0 | — |
| B | 20.5 | 32.9 |

TABLE II-continued

| Carrier Sample | Immobilized Papain Activities | |
|---|---|---|
| | Enzyme Loading, mg Papain/g Support | |
| | Initial | 83 Days Storage |
| C | 19.2 | 28.8 |

EXAMPLE II

Immobilization of Papain by Azo Coupling: Papain was immobilized to the carrier of the Sample B reaction (5%) in Table I in a second experiment using the procedure described in Example I. The immobilized enzyme in this case had an initial activity of 55 mg papain/g of immobilized enzyme.

EXAMPLE III

Immobilization of Trypsin by Azo Coupling: Trypsin was immobilized to carriers Samples A, B and C reaction solutions described in Table I using the procedure described in Example I. The immobilized enzymes had initial activities of A-3.7 mg trypsin/g immobilized enzyme; B-3.7 mg trypsin/g immobilized enzyme; C-3.9 mg trypsin/g immobilized enzyme.

EXAMPLE IV

Immobilization of Trypsin by Schiff Base Coupling: Trypsin was immobilized to the carrier of the Sample A reaction of Table I by reacting the arylamine with glutaraldehyde to form a Schiff base with a reactive aldehyde, then coupling the enzyme to the remaining aldehyde. To two grams of the Sample A carrier were added 25 mls of a 5% aqueous glutaraldehyde solution. The reaction was allowed to continue for 1 hour at room temperature, then the reaction mixture was decanted and the product was washed several times with water.

Trypsin was coupled to a similarly aldehyde-treated support by adding two ml of a solution containing 200 mg of trypsin in pH 8.5 phosphate buffer to the two grams of aldehyde-treated support. The reaction was allowed to continue in an ice bath for 2 hours, then the reaction solution was decanted. The immobilized enzyme was washed for 15 minutes with 6 M urea solution, then with water, then with 0.5 M NaCl for 15 minutes, then several more times with water. The product, assayed as described in Example I, had an initial activity of 3.6 mg trypsin.

EXAMPLE V

Immobilization of Lactase by Schiff Base Coupling on Silica:

An arylamine-silica derivative was prepared in the following manner: Five grams of porous silica (396A average pore diameter, about 120 to 200 mesh) was placed in a 20 ml column and washed by back flushing the column with water. Fifty ml of a one percent solution of the p-phenylenediamine in ethanol was then recirculated through the silica for 2 hours at room temperature. The diamine solution was drained from the column, and the support was washed with ethanol until the solution was clear and there was no adsorption when the wash solution was examined at 280 nm. The support was further rinsed with a 0.5 M NaCl solution, followed by rinsing with water to remove the salt solution.

The arylamine-silica support was reacted with glutaraldehyde by recirculating 25 ml of a 2.5% solution of glutaraldehyde in water through the column for 1 hour at room temperature. The active aldehyde support was washed with water until no glutaraldehyde was detectable in the wash water. Lactase was coupled to the aldehyde support by recirculating a solution containing 0.5 g of a crude enzyme preparation in five ml of water through the column in an upward flow for 1 hour at room temperature. The immobilized enzyme preparation was washed with a 0.5 M NaCl solution, followed by several water washings.

The immobilized lactase was assayed by transferring the product to a larger column and passing a 5% lactose solution at pH 4.0 through the column at 50° C., at a flow rate of 130 ml per hour. The activity of the immobilized enzyme was determined by measuring the amount of glucose produced in the effluent stream, using a Glucostat ® kit from Worthington Biochemical Corporation. The initial activity of the above preparation was 530 units per gram. The half-life of the immobilized enzyme was calculated by regression of the activity vs time data, assuming exponential decay. The half-life of the immobilized enzyme under the above conditions was calculated to be 45 days.

EXAMPLE VI

Immobilization of Lactase by Schiff Base Coupling on Silica:

An arylamine-silica derivative was prepared in a manner similar to that described in Example V, with the exception that a one percent solution of p-phenylenediamine in water was used for the reaction. Four grams of porous silica were washed with water in a column, and then were treated with 20 ml of a one percent (wt/vol) aqueous solution of p-phenylenediamine for 2 hours at room temperature. The support was washed successively with 20 ml of water, 300 ml of 0.5 M NaCl solution and 100 ml of water.

The arylamine-silica was reacted with 20 ml of a 2.5% glutaraldehyde solution as described in Example 5. Lactase was reacted with the active aldehyde as described above, using 0.4 g of a crude enzyme preparation in four ml of water. The immobilized enzyme, assayed as described in Example 5, had an initial activity of 439 units per gram.

Inasmuch as the subject matter of this disclosure may be readily modified, it is intended that the above examples should be deemed merely illustrative and that the scope of the disclosed invention should be limited only by the following claims.

I claim:

1. A method of bonding a biologically active protein to an inorganic support material, the method comprising the steps of:
    a. reacting a high surface area, water insoluble, inorganic support material having a surface isoelectric point less than 7.0 with a solution of p-phenylenediamine under conditions sufficient to adsorb at least a portion of the p-phenylenediamine to the surface of the support via one of the amino groups on the p-phenylenediamine, the support material having been selected from the group consisting of siliceous materials, stannic oxide, titania, manganese dioxide, and zirconia;
    b. separating the support material from the solution and washing it to remove substantially all non-adsorbed p-phenylenediamine; and
    c. reacting the separated support material with a solution of biologically active proteins under conditions sufficient to covalently bond at least a portion of the proteins to the support via the remaining available amino groups of the adsorbed p-phenylenediamine without significant loss of biological activity.

2. The method of claim 1 wherein the protein solution comprises a solution of enzymes.

3. The method of claim 1 wherein the enzymes are selected from papain, trypsin, and lactase.

4. The method of claim 1 wherein prior to the reaction of step (c) the separated product of step (b) is diazotized.

5. The method of claim 1 wherein, prior to the reaction of step (c), the separated product of step (b) is subjected to a Schiff base reaction.

6. A composite comprising biologically active proteins immobilized onto the surface of an insoluble high surface area carrier and produced in accordance with the method of claim 1.

* * * * *